US006463786B1

(12) United States Patent
Behan et al.

(10) Patent No.: US 6,463,786 B1
(45) Date of Patent: Oct. 15, 2002

(54) ODOR EVALUATION METHOD

(75) Inventors: John Martin Behan; Anne Richardson, both of Ashford; Judith Marion Annett, Helensburgh, all of (GB)

(73) Assignee: Quest International B.V., Naarden (NL)

(*) Notice: Subject to any disclaimer, the term of this patent is extended or adjusted under 35 U.S.C. 154(b) by 0 days.

(21) Appl. No.: 09/269,511

(22) PCT Filed: Sep. 27, 1997

(86) PCT No.: PCT/GB97/02651

§ 371 (c)(1),
(2), (4) Date: Jun. 9, 1999

(87) PCT Pub. No.: WO98/13808

PCT Pub. Date: Apr. 2, 1998

(30) Foreign Application Priority Data

Sep. 27, 1996 (GB) ............................................ 96307105

(51) Int. Cl.$^7$ ......................... G01N 33/497; A61B 5/08
(52) U.S. Cl. ..................... 73/23.34; 600/303; 434/236; 434/433
(58) Field of Search ............................. 73/19.01, 23.34; 434/44, 236, 239, 433, 306; 600/303, 544

(56) References Cited

U.S. PATENT DOCUMENTS

| | | | | |
|---|---|---|---|---|
| 3,795,438 A | * | 3/1974 | Westenholz et al. | 352/85 |
| 3,947,669 A | * | 3/1976 | Simmons et al. | 705/12 |
| 4,687,203 A | * | 8/1987 | Spector | 273/157 R |
| 4,762,493 A | | 8/1988 | Anderson | |
| 5,031,764 A | * | 7/1991 | Meador et al. | 206/232 |
| 5,170,780 A | * | 12/1992 | Rosenfeld | 600/544 |
| 5,227,874 A | * | 7/1993 | Von Kohorn | 705/10 |
| 5,289,389 A | * | 2/1994 | Keller | 702/116 |
| 5,759,521 A | * | 6/1998 | Hirsch | 424/47 |
| 6,104,956 A | * | 8/2000 | Naritoku et al. | 607/45 |
| 6,298,263 B1 | * | 10/2001 | Sedgwick et al. | 600/544 |

FOREIGN PATENT DOCUMENTS

| | | |
|---|---|---|
| CH | 590 530 | 8/1977 |
| FR | 2 619 511 | 2/1989 |
| FR | 2 559 931 | 8/1995 |
| WO | 89/00398 | 1/1989 |

OTHER PUBLICATIONS

Degel, J. "Implicit Memory for Odors: A Possible Method for Observation", Percept. Mot. Skills Jun. 1998, vol. 86 (No. 3 part 1), pp. 943–952.*

Willingham, D. B. "The Death of Implicit Memory", Psyche Oct. 1995, vol. 2(15). From http://psyche.cs.monash.edu.au/v2/psyche-2-15-willingham.html, pp. 1-12.*

Schab, F. R. "Odor Memory: Taking Stock", Psychological Bull. Mar. 1991, vol. 109(2), pp. 242-251.*

Wippich, W. "Implicit and Explicit Memory For Odors", Arch. Psychol. 1989, vol. 141(3), pp. 195–211.*

Wippich, W. "Recall of Odors: Naming and Autobiographical Memories Illustrate Odor Aftereffects", Z. Exp. Angew. Psychol. (Germany) 1990, vol. 37(4), pp. 679–695 and English abstract.*

Davis, Richard G. Journal of Experimental Psychology: Human Learning and Memory, 1977, vol. 3, No. 1, pp 37–51.*

Wells, F. L. American Journal of Psychology, 41, 83–86, 1929.*

Engen, Trygg. American Scientist, vol. 75, Sep.–Oct. 1987, pp 497–503.*

Spangernberg, Eric R. et al. Journal of Marketing, vol. 60, Apr. 1996, 67–90.*

Annett, Judith M. The Journal of Psychology, 130(3), May 1996, 309–319.*

Annett, Judith M and Leslie, Julian C. The Psychological Record, Summer 1995, vol. 45, 439–446.*

Soviet Inventions Illustrated Section PQ, Week 93327 Aug. 25, 1993 Derwent Publications Ltd., London, GB; AN 93–218448–27 XP002025428& SU 1 747 116 A (Pozdnyakov), Jul. 15, 1992.

* cited by examiner

*Primary Examiner*—Hezron Williams
*Assistant Examiner*—Michael Cygan
(74) *Attorney, Agent, or Firm*—Morgan, Lewis & Bockius LLP

(57) ABSTRACT

Odors are evaluated in relation to a target or priming stimulus by testing a subject by presenting the subject with one or more adors under different conditions, at least some being in the presence of one or more targets or priming stimuli; subsequently testing recognition of said one or more adors by the subject and monitoring implicit ador memory; and evaluating the results of implicit memory for ador/target combinations presented to the subject in the first stage of testing. Evaluation of the results of implicit memory for ador/target combinations presented to the subject provides a measure of the degree of association between the ador and target in a particular ador/target combination. These measures can be compared and used as a basis for ador selection.

10 Claims, No Drawings

ODOR EVALUATION METHOD

This application is the national phase of international application PCT/GB97/02651 filed Sep. 27, 1997 which designated the U.S.

FIELD OF INVENTION

This invention relates to odour evaluation and odour selection.

BACKGROUND TO THE INVENTION

In designing a new fragrance many considerations have to be taken into account. First and foremost is the need to have an aesthetically acceptable and safe blend of odorous ingredients which perform adequately in the product form which will be used by consumers. However, it is increasingly important that a fragrance is also designed as far as possible to support the intended market positioning and emotional values of a product. For example, the odour may be required to be compatible with and appropriate for a "caring/reassuring" positioning or to connote "fresh, clean, invigorating". Achieving these objectives lies within the skill and experience of skilled perfumers and perfumery experts, supported by consumer research and related fields. Nevertheless, despite the combined best efforts of all involved it is still remarkably difficult to design and select successful fragrances, particularly in new odour areas.

It is particularly difficult to gain an understanding of how consumers will perceive a fragrance in terms of positioning in advance of launching a product. Some associations can be probed by consumer research techniques such as surveys and focus groups. These improve our understanding of product attributes and consumer attributes, preferences and sensitivity. However, it is likely there will be also implicit, non-conscious associations which the consumer will not be able or willing to verbalise spontaneously and which could elude even the most probing questioning. The objective of this invention is to probe these implicit associations as a basis to aid odour selection and fragrance design.

It is well known that recognition by a person of, for example, an object may be facilitated by the person having seen the object previously, and traditional measures of memory and learning such as free recall and recognition testing can be regarded as assessing such recognition explicitly. This is because explicit memory testing relies on direct instructions to make conscious recollections about specific experiences. However, recent interest has focused on so-called implicit memory testing, using a methodology derived from the early work of Ebbinghaus (1885/1964) on savings in learning time following repeated exposure to verbal stimuli. Implicit tests do not rely on conscious recollection, and implicit learning is inferred indirectly.

One typical demonstration of implicit learning might be to ask participants to read a list of polysyllabic words (eg. fragrance) and on a later occasion ask them to fill in the blanks in word fragments to make a word (eg. fr_g_n_). Typically, participants would complete more of the fragments with list words than with non-list words and claim to be unaware of doing so. This is one example of what is known as reperition priming. Other perceptual implicit tasks include wordstem completion (eg. fra_) and perceptual identification. Conceptual implicit tests provide information that is conceptually related to the studied information but without perceptual similarity between the study and test material (eg. general knowledge questions such as "What is the largest animal on earth?"; generation of category exemplars from a category such as "four-footed animals" or viewing a degraded picture in visual studies). In addition, implicit learning might be inferred from speed or confidence in performance of given tasks.

This implicit/explicit dichotomy is also apparent in the performance of amnesic patients, who typically show impaired performance on tasks which involve explicit memory and show intact or nearly intact performance on some implicit tests. In addition, dissociative effects for explicit and implicit tasks have been demonstrated from a number of variables in normal participants. Changes in the physical format of the stimuli from study to test have a greater effect on implicit than on explicit tests, tending to reduce the priming effect in the former. Explicit and implicit tasks also are affected differently by variations in orienting instructions and sources of interference during study. In general orienting to semantic features rather than physical features facilitates performance on explicit tests more than implicit tests. Introduction of potentially interfering stimuli has a larger detrimental effect on performance of explicit tasks than on implicit tasks.

Whilst the crucial distinction between implicit and explicit memory and learning seems to be the involvement of conscious recollection, this is a descriptive distinction rather than explanatory. As Schacter (1987) noted, implicit and explicit memory "are descriptive concepts that are primarily concerned with a person's psychological experience at the time of retrieval". Theoretical accounts, whilst assuming some sort of underlying 'activation of representation' notion, emphasise either a multiple memory systems approach or a memory processes approach. System theorists define a memory system as a collection correlated functions served by anatomically distinct brain structures. By this type of account, explicit memory would, depend on what Cohen (1984) called declarative knowledge "in a system . . . in which information is . . . first processed or encoded, then stored in some explicitly accessible form for later use, and then ultimately retrieved upon demand". By contrast, implicit memory would be said to utilise procedural knowledge which is involved when "experience serves to influence the organisation of processes that guide performance without access to the knowledge that underlies the performance". Alternatively, processing theorists assume that the mental steps involved in accessing memories differ for different task types, and that assumptions about multiple memory systems are unwarranted.

Regardless of the mechanics involved, substantial behavioural data on visual and verbal memory has been accumulated. Despite an extensive literature on implicit memory, and the development of increasingly subtle implicit test procedures, it is only recently that attempts to demonstrate priming effects for odour have been reported. Schab and Crowder (1995) reported the first experiments in odour priming. In their first experiment they examined speed and accuracy of odour identification (naming). They found that presentation of common odours together with the name of the odour enhanced both the speed and accuracy of subsequent odour identification as compared with initial presentation of the odour name only. However, the observed benefit was weak compared with analogous effects in other modalities, such as identification of pictures of common objects. This was the only experiments to show a strong priming effect. The remaining experiments led Schab and Crowder to conclude that after multiple experiments, demonstration of implicit memory for odours was elusive and inconsistent.

The present inventors have now carried out further experiments that demonstrate that implicit memory does exist for odours, as can be shown by implicit memory testing, eg speed of response and confidence in response in subsequent odour recognition tests. These new experiments replicate and extend the successful Schab and Crowder priming experiment noted above. Schab and Crowder compared the effects of presenting an odour along with its name to presenting the odour name only on subsequent suprathreshold odour identification. As already noted, both speed and accuracy of naming of odours was enhanced by prior presentation of the odours. We compared the effects of prior presentation of odours under several presentation conditions on speed, accuracy and confidence in both odour identification and recognition. In other words, we examined priming of both explicit tests and implicit measures. Specifically, the presentation conditions were odour plus name, odour only, odour name only, and odour with verbal suppression. The last condition was an attempt to introduce a pure odour condition, eliminating the possibility of non-perceptual, semantic encoding of the odours. Inclusion of this condition and the simple odour only condition addressed criticisms of Schab and Crowder's failure to include a non-semantic presentation.

The new results demonstrates that the implicit measures, speed and confidence of response, reflect odour priming performed more effectively than explicit measures such as naming (identification) or correct judgement that an odour had been presented previously (recognition test).

The present invention is based on the demonstration that implicit memory does exist for odours and the recognition that this can be exploited in odour evaluation and odour selection.

SUMMARY OF THE INVENTION

In one aspect the present invention provides a method of odour evaluation for evaluating an odour in relation to a target or priming stimulus, comprising testing a subject by presenting the subject with one or more odours under different conditions, at least some being in the presence of one or more targets or priming stimnuli; subsequently testing recognition of said one or more odours by the subject and monitoring implicit odour memory; and evaluating the results of implicit memory for odour/target combinations presented to the subject in the first stage of testing.

The present invention is based on the presumption that if there is some sort of association or mental link (at least at a subconscious level and possibly not at a conscious level) in the mind of the subject between an odour being tested and a simultaneously presented target, then that odour will be better remembered (at least at a subconscious level) than would otherwise be the case. This improved memory of the odour can be tested and demonstrated by subsequent odour recognition tests, particularly as measured by implicit memory tests, which monitor subconscious or innate associations. Those odours best remembered, as indicated by implicit memory tests, are those having some sort of link or association with the, simultaneously presented target.

Evaluation of the results of implicit memory for odour/target combinations presented to the subject can thus provide a measure of the degree of association between the odour and target in a particular odour/target combinations. These measures can be compared and used as a basis of odour selection, as will be described below.

The target or priming stimulus will generally be visual or auditory in nature. A visual target may be in the form of one or more photographs, drawings, colours, written words, phrases or logos or other still images, a film or video sequence, or one or more objects, in each case possibly depicting or representing a product (eg soap powder, shampoo etc), a setting (eg a happy domestic scene), an environment (eg a bathroom environment), a relationship (eg a mother and baby), an emotion or mood (eg happiness), an outdoor scene (eg a mountain scene), an activity (eg a cricket match) etc. An auditory target may be in the form of, eg, spoken words, a musical phrase or sequence, a sound effect, a conversation, animal sounds etc.

The odour or odours under test may, for instance, be fragrances or fragrance components. In the latter case, a final fragrance may be built up from one or more components selected in relation to a particular target with the aid of the invention Tests will typically be carried out on a plurality of different subjects, and the results of the tests analysed and combined to give overall test results.

The method may be used to select from a range of several odours, eg 20, 30 or more, the odour or odours most appropriate to a particular target. Alternatively, one odour can be tested in relation to a range of several, eg 20, 30 or more, different targets to find the most appropriate odour/target combination or combinations.

Implicit odour memory can be tested, as noted above, for example by monitoring speed of response and subject confidence of accuracy of response in the subsequent step of odour recognition. Speed of response can be measured quantitatively, and this does not require the knowledge and/or cooperation of the tester, thus generating an objective, quantitative measure of implicit memory. Monitoring confidence of response requires input from the subject, eg by assessing confidence level, for instance on a numerical scale, eg of 1 to 7. This again provides a quantitative result. The results of both speed and confidence tests can be combined using a suitable formula to give an overall quantitative evaluation of implicit odour memory for each odour/target combination. The approach also has the advantage that it is not necessary to use trained or skilled subjects; naive subjects can be used, who will not be biased by prior testing experience.

The odour evaluations for different odour/target combinations can be compared and used as a basis of odour selection, to enable or assist selection of an odour or odours intended for a particular purpose, eg for use in a fragrance for a particular product. For example, the invention can be used to identify the odour or odours indicated by implicit memory testing as having the greatest degree of subconscious association with a particular target such as a product. The selected odour or odours can then be used in any desired way in relation to the target, eg in formulating a fragrance for a target product.

The present invention thus provides a method of odour selection for selecting an odour to match a particular target or priming stimulus, comprising evaluating a number of odour/target combinations by the odour evaluation method of the invention, and selecting the odour/target combination or combinations indicated as having the greatest degree of association.

The present invention also provides a product perfumed with a fragrance comprising one or more odours selected by the method of the invention using the product or other desired attribute as a target.

The invention will be further described, by way of non-limiting illustration, in the following examples, with example 1 being in the form of details of an experiment to demonstrate implicit memory for odours and odour priming.

EXAMPLE 1

The following odours were used in the experiment:
1. Strawberry jam
2. Cheese
3. Crisps (cheese and onion)
4. Tomato ketchup
5. Aftershave
6. Female perfume
7. Almond
8. Nutmeg
9. Cedar
10. Cinnamon
11. Lemon
12. Aniseed
13. Rose
14. Animal
15. Wintergreen
16. Rosemary
17. Chocolate
18. Lavender
19. Spices (mixed spice)
20. Whiskey
21. Pine (brand name cleaner)
22. Shoe polish
23. Vinegar
24. Peanuts (KP roasted)
25. Rubber bands
26. Cigarettes (ash)
27. Acetone
28. Beer
29. Coffee (liquid)
30. Johnsons baby powder
31. Pear drops
32. Mint
33. Burnt toast
34. Cucumber
35. Methylated spirits
36. Orange
37. Apple
38. Garlic
39. Tobacco
40. Banana
41. Petrol
42. Salmon (tinned)
43. Bleach
44. Onion (chopped)
45. Saddle leather Each odour was placed in a respective polystyrene cup and concealed with a crumpled piece of aluminium foil placed inside the top of the cup.

For each subject the odours were allocated to a presentation condition and the condition used for each odour was randomised from subject to subject except for the "control" condition for which samples 37 to 45 were always used. The 5 presentation conditions were:

1. Odour+name—the subject was presented with an odour to smell and at the same time shown a card with the odour name written on it.
2. Odour only—the subject was presented only with the odour to smell.
3. Odour name only—the subject was shown a card with the odour name written on it and given a blank or odour-free pot to smell.
4. Odour+suppression—headphones were placed over the subject's ears and they were played a tape on which digits were recited. The subjects were asked to repeat each digit as it was played. At the same time the odours were presented for the subjects to smell. This condition introduced a pure odour condition, eliminating the possibility of non-perceptual, semantic encoding of the odours.
5. Control—subjects were not presented with these odours in the first phase of the experiment.

The order of presentation of the odours was randomised for each subject but all of the "Suppression" conditions were presented consecutively for practical reasons.

The experiment was carried out in two phases. In the first phase the odours were presented in the various conditions as described above and in between each presentation the subject was asked to write down the sample number and record his or her assessment of the sample for pleasantness and familiarity on a 7 point scale. This task was included as a distracter for the subjects.

After a break of 10 minutes, in the second phase of the experiment all of the odours were presented to the subject in random order and the subject was asked to complete a questionnaire indicating:

1. Had they smelt the odour in the first phase of the experiment (yes/no).
2. How confident were they that they had answered correctly (on a 7 point scale from "guess/unsure" to "very confident").
3. The name of the odour.

At the same time, unknown to the subject, the time taken to answer question 1 was recorded.

The experiment was carried out over 2 days during which a total of 14 subjects were tested.

Details of Results

1. Correct Recognition Responses (Explicit Test)
Average number of correct recognition responses:

| | |
|---|---|
| Control | 7.29 |
| Odour + name | 6.93 |
| name only | 6.36 |
| odour only | 5.93 |
| odour + suppression | 4.86 |

Paired comparison parametric T-test results

| | | | |
|---|---|---|---|
| odour + name > odour only | t = 2.25 | p = 0.02 | Sig |
| odour + name > odour + suppression | t = 3.03 | p = 0.004 | Sig |
| odour + name > name only | t = 1.07 | p = 0.15 | NS |
| odour + name < control | t = −0.8 | p = 0.22 | NS |
| odour only > odour + suppression | t = 1.01 | p = 0.066 | NS |
| odour only < name only | t = −0.8 | p = 0.21 | NS |
| odour only < control | t = −3.8 | p = 0.0011 | Sig |
| odour + suppression < name only | t = −2.24 | p = 0.024 | Sig |
| odour + suppression < control | t = −3.54 | p = 0.0017 | Sig |
| name only < control | t = −2.06 | p = 0.029 | Sig |

Little evidence for odour priming is shown in terms of significant differences between conditions, but the order of the conditions is as might be predicted. In particular odour+ name is better than name only, but the difference is not statistically significant. Also there is evidence for name only priming, ie. odour, +name is better than odour only and odour+suppression. The odd finding was the high performance on the control, ie not previously presented odours. The explanation may lie in the participant variables.

2. Correct Identification (Naming) Responses (Explicit Test)

Average number of correct responses

| | |
|---|---|
| odour + name | 6.14 |
| odour only | 4.64 |
| name only | 4.14 |
| odour + suppression | 4.0 |
| control | 3.43 |

Paired comparison parametric T-test

| | | | |
|---|---|---|---|
| odour + name > odour only | t = 2.62 | p = 0.010 | Sig |
| odour + name > odour + suppression | t = 3.85 | p = 0.004 | Sig |
| odour + name > name only | t = 4.266 | p = 0.00045 | Sig |
| odour + name > control | t = 5.87 | p = 0.0000273 | Sig |
| odour only > odour + suppression | t = 0.93 | p = 0.18 | Sig |
| odour only > name only | t = 0.889 | p = 0.19 | NS |
| odour only > control | t = 2.406 | p = 0.0158 | Sig |
| odour + suppression < name only | t = 0.245 | p = 0.405 | NS |
| odour + suppression > control | t = 1.169 | p = 0.13 | NS |
| name only > control | t = 1.540 | p = 0.07 | NS |

There is evidence for odour priming where odour+name is better than name only (significant); odour+name is better than control (significant); odour only is better than the control (significant); odour+suppression is better than control (not significant).

3. Confidence (Implicit Test)

If priming occurs we expect that confidence will be higher on correct responses when the odour was previously presented and lower on incorrect responses (ie when getting it wrong there is greater degree of doubt (an unconscious feeling of knowing that the response might not be correct)).

3.1. Summary of Confidence Ratings for Recognition when Recognition was Correct (Irrespective of Naming Response)

| | |
|---|---|
| odour + name | 5.69 |
| odour only | 5.585 |
| odour + suppression | 5.379 |
| control | 4.83 |
| name only | 4.28 |

T-test pairwise comparison

| | | |
|---|---|---|
| odour + name > odour only | NS | |
| odour + name > odour + suppression | p = 0.057 | NS |
| odour + name > name only | p = 0.0011 | Sig |
| odour + name > control | p = 0.009 | Sig |
| odour only > odour + suppression | NS | |
| odour only > name only | p = 0.002 | Sig |
| odour only > control | p = 0.0089 | Sig |
| odour + suppression > name only | p = 0.0012 | Sig |
| odour + suppression > control | p = 0.072 | NS |
| name only < control | p = 0.08 | NS |

For odour+name subjects were more confident than for name only and control (both significant). For odour only subjects were more confident than for name only and control (both significant). For odour+suppression (ie. pure odour condition) confidence results were better than for name only (significant) and better than for control (not significant but marginal, p+0.072).

3.1. Summary of Confidence Ratings for Recognition when Recognition was Incorrect (Irrespective of Naming Response)

| | |
|---|---|
| odour + name | 2.84 |
| odour + suppression | 3.54 |
| odour only | 3.83 |
| control | 4.41 |
| name only | 4.79 |

T-test pairwise comparison

| | | |
|---|---|---|
| odour + name < odour only | p = 0.07 | NS |
| odour + name < odour + suppression | | NS |
| odour + name < name only | p = 0.0027 | Sig |
| odour + name < control | p = 0.0247 | Sig |
| odour only > odour + suppression | | NS |
| odour only < name only | p = 0.068 | NS |
| odour only < control | | NS |
| odour + suppression < name only | p = 0.016 | Sig |
| odour + suppression < control | p = 0.058 | NS |

These results show the predicted pattern (almost). For odour+name subjects were less confident than for name only and control (both significant) ie. "I'm saying I haven't smelt this one before but I'm not sure about it". For odour only subjects were less confident than for name only (not significant but marginal, p=0.068). For odour+suppression (pure odour) subjects were less confident than for name only and control (both significant).

4. Response Time (Implicit Test)

A similar pattern would be predicted as for the confidence test, but perhaps not as clear cut, as subjects could be more variable. The results (below) show some evidence for this effect.

4.1 Timings for Recognition Response when the Response was Correct Irrespective of Naming Response

| | |
|---|---|
| odour only | 2.90 |
| odour + name | 3.04 |
| odour + suppression | 3.44 |
| control | 3.69 |
| name only | 3.97 |

T-test pairwise comparison

| | | |
|---|---|---|
| odour + name > odour only | | NS |
| odour + name < odour + suppression | p = 0.03 | Sig |
| odour + name < name only | p = 0.005 | Sig |
| odour + name < control | p = 0.001 | Sig |
| odour only < odour + suppression | p = 0.017 | Sig |
| odour only < name only | p = 0.005 | Sig |
| odour only < control | p = 0.001 | Sig |
| odour + suppression < name only | p = 0.079 | NS |
| odour + suppression < control | p = 0.094 | NS |
| name only > control | | NS |

For odour+name response was faster than for name only and control (both significant). For odour only response was faster than for name only and control (both significant). For odour+suppression response was faster than for name only and control (not significantly but p=0.079 and 0.094, respectively).

4.2 Timings for Recognition Response when the Response was Incorrect Irrespective of Naming Response

| | |
|---|---|
| odour + name | 4.86 |
| odour only | 4.27 |
| odour + suppression | 4.21 |
| control | 3.52 |
| name only | 3.45 |

T-test pairwise comparison

| | | |
|---|---|---|
| odour + name > odour only | | NS |
| odour + name > odour + suppression | | NS |
| odour + name > name only | p = 0.069 | NS |
| odour + name > control | | NS |
| odour only > odour + suppression | | NS |
| odour only > name only | p = 0.088 | NS |
| odour only > control | | NS |
| odour + suppression > name only | p = 0.036 | Sig |
| odour + suppression > control | p = 0.057 | NS |
| name only < control | | NS |

For odour+name response was slower than for name only and control (not significant but p for name only is 0.069). For odour only response was slower than for control (non significant but p=0.057).

Conclusion

There is convergent evidence for odour priming particularly in implicit measures.

EXAMPLE 2

In a second example, a series of odours were tested generally as described in example 1, but with only a series of primary stimuli presented in the first phase of the experiment. In the second phase, similar implicit memory tests were used to identify those odours for which primary stimuli was demonstrated. This was used as a basis for odour selection.

What is claimed is:

1. A method for selecting an odour to match a particular target or priming stimulus, comprising evaluating a number of odour/target combinations by presenting to a plurality of subjects one or more odours under different conditions, at least one of said conditions being presentation of the odour under verbal suppression and at least some of said conditions being in the presence of one or more targets or priming stimuli, said condition of verbal suppressing representing a pure odour condition reducing the possibility of non-perceptual, semantic encoding of odours, subsequently testing recognition of said one or more odours by the subjects and monitoring implicit odour memory by, evaluating the results of implicit memory by comparing speed of response and confidence in response for odour/target combinations presented to the subjects and thereafter selecting on the basis of said evaluation the odour/target combination or combinations indicated as having the greatest degree of subconscious association.

2. A method according to claim 1, wherein the target is visual or auditory in nature.

3. A method according to claim 2, wherein the target comprises one or more photographs, drawings or other still images, a film or video sequence, or one or more objects.

4. A method according to claim 2, wherein the target comprises spoken words, a musical phrase or sequence, a sound effect, a conversation, animal sounds.

5. A method according to claim 1, wherein the odour or odours under test comprise fragrances or fragrance components.

6. A method according to claim 1, wherein the results of the tests are analysed and combined to give overall tests results.

7. A method according to claim 1, wherein implicit odour memory is tested by monitoring speed of response and subject confidence of accuracy of response in the subsequent step of odour recognition.

8. The method of claim 1 wherein at least one of said conditions includes presentation of the odour only.

9. A method of making a perfumed product, comprising mixing with the product one or more odours selected by the method of claim 1 using the product or other desired attribute as a target.

10. A method of making a fragrance matched to a particular target or prining stimulus, comprising mixing one or more odours selected in relation to the target by the method of claim 1.

* * * * *

UNITED STATES PATENT AND TRADEMARK OFFICE
CERTIFICATE OF CORRECTION

PATENT NO.    : 6,463,786 B1                                           Page 1 of 1
DATED         : October 15, 2002
INVENTOR(S)   : Behan et al.

It is certified that error appears in the above-identified patent and that said Letters Patent is hereby corrected as shown below:

<u>Title page,</u>
Item [22], should read -- PCT Filed:  26 September 1997 --

Signed and Sealed this

Sixteenth Day of December, 2003

JAMES E. ROGAN
*Director of the United States Patent and Trademark Office*